(12) United States Patent
Heikenfeld

(10) Patent No.: US 11,857,313 B2
(45) Date of Patent: Jan. 2, 2024

(54) SWEAT BIOSENSING COMPANION DEVICES AND SUBSYSTEMS

(71) Applicant: University of Cincinnati, Cincinnati, OH (US)

(72) Inventor: Jason C. Heikenfeld, Cincinnati, OH (US)

(73) Assignee: University of Cincinnati, Cincinnati, OH (US)

(*) Notice: Subject to any disclaimer, the term of this patent is extended or adjusted under 35 U.S.C. 154(b) by 672 days.

(21) Appl. No.: 16/645,952

(22) PCT Filed: Sep. 11, 2018

(86) PCT No.: PCT/US2018/050400
§ 371 (c)(1),
(2) Date: Mar. 10, 2020

(87) PCT Pub. No.: WO2019/051471
PCT Pub. Date: Mar. 14, 2019

(65) Prior Publication Data
US 2020/0275864 A1    Sep. 3, 2020

Related U.S. Application Data

(60) Provisional application No. 62/556,707, filed on Sep. 11, 2017.

(51) Int. Cl.
*A61B 5/145* (2006.01)
*A61B 5/00* (2006.01)

(52) U.S. Cl.
CPC ........ *A61B 5/14517* (2013.01); *A61B 5/1451* (2013.01); *A61B 5/14503* (2013.01); *A61B 5/14532* (2013.01); *A61B 5/6802* (2013.01)

(58) Field of Classification Search
None
See application file for complete search history.

(56) References Cited

U.S. PATENT DOCUMENTS

2006/0004271 A1   1/2006  Peyser et al.
2007/0027383 A1*  2/2007  Peyser .................. G01N 33/66
                                                        600/362

(Continued)

FOREIGN PATENT DOCUMENTS

WO       2017019602 A1    2/2017

OTHER PUBLICATIONS

Heikenfeld. Non-invasive Analyte Access and Sensing through Eccrine Sweat: Challenges and Outlook circa 2016. Electroanalysis 2016, 28, 1242-1249. (Year: 2016).*

(Continued)

*Primary Examiner* — Etsub D Berhanu
(74) *Attorney, Agent, or Firm* — Wood Herron & Evans LLP

(57) ABSTRACT

A system 100, 200 for sensing one or more analytes in a first biofluid and a second biofluid and methods of using said system. The system 100, 200 may include a first subsystem 102, 200a, 200b with a first sensor 120, 122, 220, 222 for sensing a first analyte in the first biofluid and a second subsystem 104, 200b, 200c with a second sensor 124, 126, 222, 224 for sensing a second analyte in the second biofluid. The second analyte may be the same as or different from the first analyte and the second biofluid may be different from the first biofluid. In an embodiment, the first biofluid is a non-sweat biofluid and the second biofluid is sweat. The system 100, 200 may be used to detect lag time for measuring an analyte in one of the biofluids.

6 Claims, 1 Drawing Sheet

(56) References Cited

U.S. PATENT DOCUMENTS

2008/0081969 A1\* 4/2008 Feldman .............. A61B 5/0024
600/322
2012/0108931 A1\* 5/2012 Taub ...................... G16H 20/10
600/347

OTHER PUBLICATIONS

International Search Report and Written Opinion in International Patent Application No. PCT/US2018/050400, dated Dec. 19, 2018, 11 pgs.

\* cited by examiner

SWEAT BIOSENSING COMPANION DEVICES AND SUBSYSTEMS

BACKGROUND

Non-invasive biosensing technologies have enormous potential for applications ranging from athletics, to neonatology, to pharmacological monitoring, to personal digital health, to name a few applications. The sweat ducts can provide a route of access to many of the same biomarkers, chemicals, or solutes that are carried in blood and can provide significant information enabling one to diagnose ailments, monitor health status, detect toxins, and monitor performance and other physiological attributes prior to other physical signs or symptoms. Sweat has many of the same analytes and analyte concentrations found in blood and interstitial fluid. Interstitial fluid has even more analytes at high concentrations than sweat does, especially for larger sized and more hydrophilic analytes such as proteins.

One challenge with sensing interstitial fluid is the lag time of sensor readings. Because the dermis itself does not require support of a very high amount of metabolic activity, its turnover rate for interstitial fluid is very slow (e.g., 10-30 minutes). Many sensors, be they needles, microneedles, implanted sensors in the dermis, or other biofluid compartments in the body, will therefore have sensor responses that lag behind blood concentration. For example, glucose sensors based on implanted needles can have a lag time of 10-20 minutes, and microneedle sensors that rely on diffusion of glucose to the sensor can be even slower and on the order of 20-30 minutes. Furthermore, continuous sensing could be challenging for implanted devices. For example, such devices would need to sample and sense in discrete samplings (e.g., non-continuous).

Eccrine sweat glands are also bathed in interstitial fluid, and many of the analytes found in sweat are transported into sweat by pathways such as paracellular pathways through the lining of the sweat gland. Analyte concentrations in sweat glands, however, can in some cases have much less lag time behind the changes of analyte concentrations in blood, as fast as 1-3 minutes depending on analyte and sweat generation rate.

SUMMARY

Many of the drawbacks and limitations stated above can be resolved by creating novel and advanced interplays of chemicals, materials, sensors, electronics, microfluidics, algorithms, computing, software, systems, and other features or designs, in a manner that affordably, effectively, conveniently, intelligently, or reliably brings sensing technology into intimate proximity with biofluid and analytes as they emerge from the blood compartment and into biofluid compartments such as interstitial fluid.

Advanced microfluidics and sensor integration strategies can allow sweat transport to sensors in just several minutes. Therefore, sweat biosensing as a companion device or subsystem for devices for sensing analytes in non-sweat biofluids could provide a potential method to correct for or mitigate the disadvantages of the lag time experienced for sensing analytes directly in non-sweat biofluids like interstitial fluid. Therefore, a sweat sensing device, which can sense sweat continuously, could be an advantageous companion device by providing continuous data. One might ask why not simply use sweat by itself for sensing the analyte, and why bother with needle, implanted, or other techniques necessary for detecting analytes in non-sweat biofluids? Detecting analytes in sweat alone may not always be superior to detecting analytes in non-sweat biofluids. For example, glucose and proteins in sweat are dilute compared to their concentrations in interstitial fluid. Furthermore, measuring biomarker panels in a temporal fashion can be limited if only a biofluid such as interstitial fluid is used, or if only sweat is utilized. Simultaneous measurements of analytes in one or more non-sweat biofluids alone or in combination with analytes in sweat may be advantageous.

Embodiments of the disclosed invention provide biofluid sensing devices capable of providing superior biosensing by coupling higher precision or accuracy concentration sensing of analytes in a non-sweat biofluid such as interstitial fluid with more rapid trending and continuous data provided by sensing of analytes in sweat.

BRIEF DESCRIPTION OF THE DRAWINGS

The objects and advantages of the disclosed invention will be further appreciated in light of the following detailed descriptions and drawings in which.

DEFINITIONS

Figure 1:
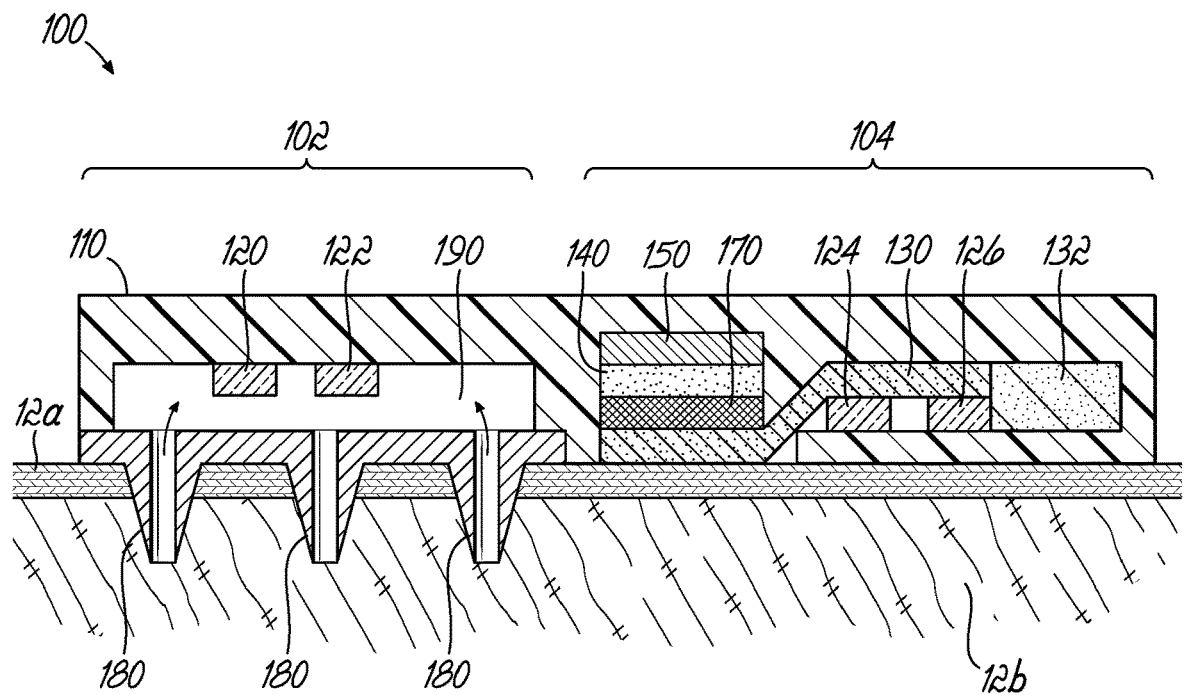
FIG. 1 is a cross-sectional view of a portion of a wearable device for biosensing based on subsystems for measurement of analytes in interstitial fluid and for analytes in sweat.

As used herein, "non-sweat biofluid" or "biofluid that is not sweat" means a fluid source of analytes that is not sweat. For example, a non-sweat biofluid could be a solution that bathes and surrounds tissue cells such as interstitial fluid. Embodiments of the disclosed invention may focus on interstitial fluid found in the skin and, particularly, interstitial fluid found in the dermis. However, interstitial fluid in other body compartments may also apply. Sensors could also be implanted in large arteries, the bladder, or other biofluid cavities, such that the term non-sweat biofluid may also apply to biofluids such as blood, urine, saliva, or other suitable biofluids for analyte sensing that are not sweat.

As used herein, "sweat" is a fluid source of analytes that is sweat from eccrine or apocrine glands. Sweat from eccrine glands may be easier to sense as apocrine glands are harder to access in their locations on the body, less controlled in sweat generation rate, and contain confounding challenges such as high bacterial counts, which can skew analyte readings.

As used herein, "continuous monitoring" means the capability of a device to provide at least one measurement of a biofluid, such as interstitial fluid, determined by a continuous or multiple collection and sensing of that measurement or to provide a plurality of measurements of that biofluid over time.

As used herein, "chronological assurance" is an assurance of the sampling rate for measurement(s) of a biofluid, such as sweat or a non-sweat biofluid like interstitial fluid, or solutes therein in terms of the rate at which measurements can be made of new biofluid or its new solutes as originating from the body. Chronological assurance may also include a determination of the effect of sensor function, potential contamination with previously generated biofluids, previously generated solutes, other fluid, or other measurement contamination sources for the measurement(s).

As used herein, "sampling rate" is the effective rate at which new biofluid or new solute concentrations reach a sensor that measures a property of the biofluid such as sweat or a non-sweat biofluid or the solutes therein. Sampling rate therefore could be the rate at which new biofluid is refreshed at the one or more sensors and therefore old fluid is removed as new fluid arrives. The inverse of sampling rate (1/s) could also be interpreted as a "sampling interval". Sampling rates or intervals are not necessarily regular, discrete, periodic, discontinuous, or subject to other limitations.

As used herein, "measured" can imply an exact or precise quantitative measurement and can include broader meanings such as, for example, measuring a relative amount of change of something. Measured can also imply a binary measurement, such as 'yes' or 'no' type measurements.

As used herein, "advective transport" is a transport mechanism of a substance or conserved property by a fluid due to the fluid's bulk motion.

As used herein, "diffusion" is the net movement of a substance from a region of high concentration to a region of low concentration. This is also referred to as the movement of a substance down a concentration gradient.

As used herein, "convection" is the concerted, collective movement of groups or aggregates of molecules within fluids and rheids, either through advection or through diffusion or a combination of both.

DETAILED DESCRIPTION

Embodiments of the disclosed invention apply at least to any type of sensor device that measures biofluid or analyte in a biofluid such as sweat, a non-sweat biofluid, or a combination of both sweat and a non-sweat biofluid. Further, embodiments of the disclosed invention apply to sensing devices, which can take on forms including adhesive patches, bands, straps, implants, transdermal patches, portions of clothing, wearables, or any suitable mechanism that reliably brings sensing technology into intimate proximity with a non-sweat biofluid, sweat, or both a non-sweat biofluid and sweat.

Certain illustrated embodiments of the disclosed invention show sensors as simple individual elements. It is understood that many sensors require two or more electrodes, reference electrodes, or additional supporting technology or features which are not captured in the description herein. In embodiments, sensors are preferably electrical in nature, but may also include optical, chemical, mechanical, or other known biosensing mechanisms. Sensors can be in duplicate, triplicate, or more, to provide improved data and readings. Sensors may be referred to by what the sensor is sensing, for example: a sweat sensor; an impedance sensor; a sample volume sensor; a sample generation rate sensor; and a solute generation rate sensor. Certain embodiments of the disclosed invention show sub-components of what would be sensing devices with more sub-components needed for use of the device in various applications, which are obvious (such as a battery, antenna, adhesive), and for purposes of brevity and focus on inventive aspects, such components are not explicitly shown in the diagrams or described in the embodiments of the disclosed invention.

Embodiments of the disclosed invention provide biofluid sensing systems capable of providing superior biosensing by coupling higher precision or accuracy concentration sensing of analytes in a first biofluid with more rapid trending and continuous data provided by sensing analytes in a second biofluid. In an exemplary embodiment the first biofluid may be a non-sweat biofluid and the second biofluid may be sweat.

With reference to FIG. 1, in an embodiment of the disclosed invention, a biofluid sensing system comprises a single device 100 that includes two subsystems 102, 104 for sensing analytes in different types of biofluids such as a sweat or a non-sweat biofluid or both. The device 100 is placed on or near skin 12, which includes the epidermis 12a and dermis 12b. The dermis 12b contains interstitial fluid. The device 100 may utilize any suitable substrate or material to hold it together, for example, such as a plastic nylon casing 110. The device 100 contains sensors 120, 122, 124, 126, each of which could be any sensor capable of measuring a property of a biofluid or an analyte in a biofluid. For example, each of the sensors 120, 122, 124, 126 may be an ion-selective senor, an amperometric (enzymatic) sensor, an electrochemical aptamer sensor, a fluorometric sensor, an antibody-based sensor, or may involve other suitable sensing modalities. As shown, each subsystem has a group of sensors, and each sensor in the group may be configured to sense the same or different analytes in a single type of biofluid. In the illustrated embodiment, sensors 120, 122 are grouped together and sensors 124, 126 are grouped together. It should be recognized that the number of sensors in each group of sensors may vary.

Each of the sensors 120, 122, 124, 126 may be for sensing the same or different analytes in one or more than one type of biofluid. In the illustrated embodiment, sensors 120, 122 are for sensing analytes in a non-sweat biofluid such as interstitial fluid, and sensors 124, 126 are for sensing analytes in sweat. In that regard, the device 100 includes first subsystem 102 for sensing analytes in interstitial fluid that comprises a microneedle array 180 that provides a pathway 190 for diffusion of analytes between the dermis 12b and the sensors 120, 122. If the pathway 190 is initially dry, biofluid may also enter into the pathway 190 through the microneedle array 180 such that the analyte diffuses through the biofluid inside pathway 190 to the sensor. In another embodiment, pathway 190 may be preloaded with a fluid that allows analytes in the biofluid to diffuse from the microneedle array 180 through the fluid in pathway 190 to the sensors 120, 122. The microneedle array 180 can comprise any suitable material used for fabrication of microneedle arrays, such as glass, silicon, skin-compatible metals, polymers, etc. The device 100 also includes a subsystem 104 for sensing analytes in sweat comprising a wicking component or microfluidic channel 130 to transport sweat generated on the skin 12 to the sensors 124, 126. Suitable materials for the wicking component or microfluidic channel 130 include paper, rayon, and a polymer microchannel. The subsystem 104 for sensing sweat further includes a reservoir 132 for storage of old/waste sweat, which could be for example a hydrogel. Further included in the subsystem 104 for sensing sweat is a sweat stimulating component comprising a membrane 170, a sweat stimulation gel or solution 140, and an iontophoresis electrode 150 to drive sweat stimulants from the stimulation gel or solution 140 into the skin 12. The stimulation gel 140 may be, for example, agar containing sweat stimulants such as pilocarpine or carbachol. Suitable materials for the membrane 170 include a forward osmosis membrane or a dialysis membrane. The membrane 170 serves to decrease fluid and or solution contamination and mixing between the stimulation gel or solution 140, the skin 12, and the microfluidic component 130.

Still referring to FIG. 1, the device 100 may be applied to the skin 12. The microneedle array 180 pierces the skin 12 to provide the pathway 190 for diffusion of analytes in a non-sweat biofluid between the dermis 12b and the sensors 120, 122. The sensors 120, 122 sense the same or different analytes that diffuse through the microneedle array 180 into the pathway 190. Additionally, the sweat sensing subsystem 104 may stimulate sweat thereunder by iontophoretically driving the sweat stimulant from the stimulation gel or solution 140 through the membrane 170 and microfluidic channel 130 into the skin 12 using the iontophoresis electrode 150. As sweat emerges from the skin 12, the microfluidic channel 130 transports sweat across the sensors 124, 126 and into the reservoir 132. Where the subsystems are configured to sense analytes in at least two different biofluids, an effect of lag time on the measurements of an analyte in one biofluid may be determined at least in part by the measurements of an analyte in a different biofluid. For example, sensors 120 and 122 and sensors 124 and 126 could communicate with an electronic microcontroller that could be part of the device 100. The microcontroller could communicate with a wireless communication component, such as Bluetooth, and then to a smartphone with software that could analyze the data and lag times. Applications of the device 100 are provided in the Examples below.

Figure 2:
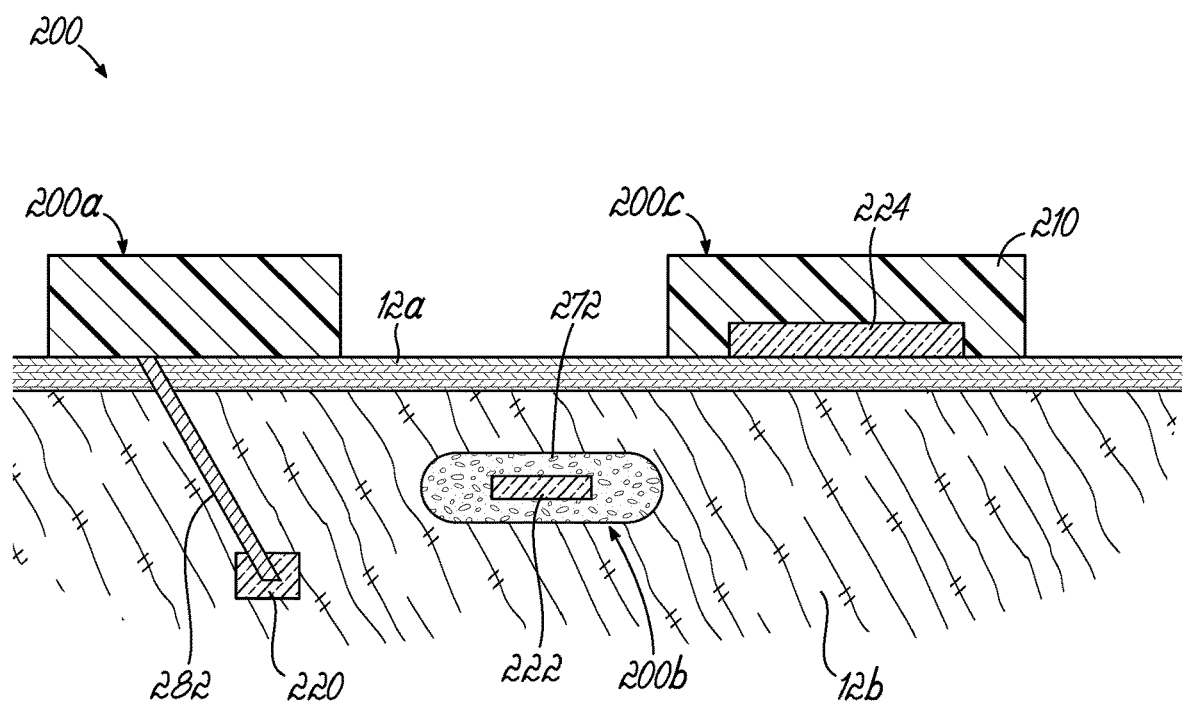
FIG. 2 is a cross-sectional view of a portion of multiple coordinated wearable or implanted devices for biosensing based on measurement of analytes in interstitial fluid and of analytes in sweat.

With reference to FIG. 2, in an embodiment of the disclosed invention, a biofluid sensing system 200 is comprised of a plurality of separate subsystems or devices 200a, 200b, 200c. The subsystem 200a is a transdermal sensor that includes a sensor 220 at the end of a needle or wire 282 that extends into the skin 12. The needle or wire 282 electrically connects the sensor 220 to the subsystem 200a, which may also include electronics and a housing, such as a plastic housing. The needle or wire 282 may be, for example, like that used for continuous wearable glucose monitors.

The subsystem 200b is an implantable sensor system that can be electronic or optical. In the illustrated embodiment, the subsystem 200b is electronic and comprises, for example, a sensing and transmission component 222, which includes a microcircuit and sensor and communication antenna, embedded in a biocompatible casing 272. The biocompatible casing 272 may be made of, for example, a hydrogel, block co-polymer, or other suitable material that is porous to the analyte of interest. In an embodiment, an optical subsystem 200b could be, for example, a fluorometric or colorimetric sensor that is optically interrogated through the epidermis 12a.

The subsystem 200c is for sensing sweat and comprises a sweat sensor 224 in a casing 210. In various embodiments, sweat may be stimulated before the subsystem 200c is applied to skin or naturally induced sweat may be utilized. Alternately, sweat stimulation could be integrated into 200c using suitable approaches such as the approach show for the device 100.

While the embodiment illustrated in FIG. 2 includes three types of sensor subsystems 200a, 200b, 200c, embodiments of the invention may include two of the three types of illustrated sensor subsystems. For example, an embodiment of the invention may include subsystem 200a and subsystem 200b or subsystem 200c and another embodiment may include subsystem 200b and subsystem 200c. It is further contemplated that one or more of the subsystems 200a, 200b, 200c may be included in duplicate or triplicate or more.

In order to facilitate a more complete understanding of the embodiments of the invention, the following non-limiting examples of the device 100 are provided below.

Example 1

The physiological lag between glucose levels in the blood and in interstitial fluid can be problematic in continuous glucose monitoring if the lag isn't considered when calibrating the monitors. Patients with diabetes who want to use continuous glucose monitors need to be instructed to calibrate the devices when their glucose levels are in a steady state rather than during a period of changing glucose levels. Finger-stick monitors and the electrochemical sensors in continuous glucose monitors (CGMs) work on the same principle, based on glucose oxidase breaking down glucose and generating electrons, which are measured by the monitor's sensors. Finger-stick monitors measure serum glucose, and continuous monitors measure glucose in the interstitial fluid. When glucose levels are changing—such as rising glucose levels seen particularly after meals—there can be as much as a 30-minute delay before a changed glucose level in blood is reflected in interstitial fluid. If patients calibrate the continuous glucose monitoring devices when their glucose is changing (i.e., not in steady state), their sensor could be calibrated inaccurately and not give them reliable readings.

With reference to FIG. 1, the sensor 120 senses glucose in interstitial fluid whereas sensor 124 senses glucose in sweat. In an embodiment, both sensors 120, 124 include glucose oxidase enzymatic electrodes. Additionally, or alternatively, one or both of the sensors 120, 124 may be an electrochemical aptamer-based sensor for glucose. Additionally, or alternatively, one or both of the sensors 122, 126 may sense pH to account for the effects of pH on operation of the sensors 120, 124, respectively. The sensor 124 can alert the user that glucose levels are changing rapidly and warn of possible inaccurate calibration or even feed into an algorithm that provides a potential accuracy level for the calibration in numeric form, or such as 'good-fair-poor' indications. The sensor 124 could also be used to detect the rate of change in glucose during calibration, and then couple that information with the calibration data to correct for potential error in calibration. For example, if the sensor 124 measures glucose rising at 10% every 5 minutes, and the lag time for the sensor 120 is 15 minutes, then the device 100 calibration value used based on the sensor 120 can be increased by approximately 30% due to the information provided by the sensor 124. Devices and subsystems in FIG. 2 could provide similar advantages. In this example, two or more of the sensors sense the same $1^{st}$ analyte, such as glucose, with one sensor sensing the $1^{st}$ analyte in a biofluid that is not sweat and the other sensor sensing the $1^{st}$ analyte in sweat.

Example 2

With reference to FIG. 2, in an embodiment, the sensors 220, 222, 224 may each sense a different analyte. For example, the sensor 220 could be for sensing an inflammatory marker, such as cytokine, that changes slowly in the body and slowly in interstitial fluid, the sensor 222 could be a fluorometric sensor for glucose in interstitial fluid, and the sensor 224 could be a sweat sensor for cortisol. The sensor 220 could measure the longer-term effects of stressors on the body (e.g., inflammation), whereas the sensor 224 could measure the short term effects of stress on the body. For example, if a patient had a panic attack, cortisol levels could rise rapidly, and the rate of rise of cortisol as sensed by the sensor 224 could provide an indication of the severity of the panic attack. The prolonged effect of the panic attack could also be measured by sensor 220 by measuring at least one cytokine level. The glucose sensor 222 could measure the effect of diet and health on the causality of the panic attack(s). Thus, in an embodiment, two or more of the sensors are for sensing a $1^{st}$ analyte and $2^{nd}$ analyte that are different, one sensor sensing the $1^{st}$ analyte in a biofluid that is not sweat and the other sensor sensing the $2^{nd}$ analyte in sweat.

Example 3

With reference to FIG. 1, the sensor 120 senses vasopressin, and the sensor 124 senses Na+, which is an indicator of sweat generation rate. The sensor 124 could therefore provide a leading warning of possible dehydration before dehydration occurs as recorded by sensor 220, which measures changes in levels of vasopressin.

Example 4

With reference to FIG. 1, the sensors 120, 124 senses glucose, the sensor 122 senses insulin, and the sensor 126 senses adrenaline or cortisol, which are released when the body senses low glucose. This combined system could measure not only glucose like that of Example 1, but also circulating concentrations of delivered insulin, and the body's rapid response to the effects of low or high glucose, for a complete monitoring system that helps a patient or user avoid hypoglycemic shock.

While specific embodiments have been described in detail to illustrate the disclosed invention, the description is not intended to restrict or in any way limit the scope of the appended claims to such detail. The various features discussed herein may be used alone or in any combination. Additional advantages and modifications will readily appear to those skilled in the art. The invention in its broader aspects is therefore not limited to the specific details, representative apparatus and methods and illustrative examples shown and described. Accordingly, departures may be made from such details without departing from the scope of the general inventive concept.

What is claimed is:

1. A method of determining a lag time effect while sensing a first analyte in a first biofluid comprising:
   sensing the first analyte in the first biofluid with a first sensor of a device;
   sensing a second analyte in a second biofluid with a second sensor of the device, the second analyte being the same as or different from the first analyte, the second biofluid being different from the first biofluid, wherein the first biofluid is interstitial fluid and the second biofluid is sweat;
   determining a lag time effect in measurements of the first analyte in the first biofluid based at least in part on measurements of the second analyte in the second biofluid; and
   adjusting calibration of the device based on the determined lag time effect;
   wherein the determining a lag time effect and adjusting calibration steps are performed by a processor or by software.

2. The method of claim 1, wherein sensing the second analyte in the second biofluid is simultaneous with sensing the first analyte in the first biofluid.

3. The method of claim 1, wherein sensing the second analyte in the second biofluid is continuous.

4. The method of claim 1, wherein the second analyte is the same as the first analyte.

5. The method of claim 1, further comprising:
   sensing at least one additional analyte in at least one of the first or second biofluids or a property of at least one of the first or second biofluids, the at least one additional analyte being the same as or different from the first and second analytes, for correcting measurements from at least one of the first or second sensors.

6. The method of claim 1, further comprising:
   sensing a third analyte in a third biofluid, the third analyte being the same as or different from the first and second analytes,
   wherein determining the lag time effect in measurements of the first analyte in the first biofluid is further based on measurements of the third analyte in the third biofluid.

* * * * *